US00PP15594P2

(12) United States Plant Patent
Harrington

(10) Patent No.: US PP15,594 P2
(45) Date of Patent: Feb. 22, 2005

(54) ***CLEMATIS* PLANT NAMED 'BARBARA HARRINGTON'**

(50) Latin Name: *Clematis* species
Varietal Denomination: Barbara Harrington

(76) Inventor: Dominic Harrington, 46 Old Lynn Road, Wisbech (GB), PE14 7AJ ( * ) Notice: Subject to any disclaimer, the term of this patent is extended or adjusted under 35 U.S.C. 154(b) by 4 days.

(21) Appl. No.: 10/388,904

(22) Filed: Mar. 15, 2003

(51) Int. Cl.[7] ..... A01H 5/00
(52) U.S. Cl. ..... Plt./228
(58) Field of Search ..... Plt./228

(56) References Cited

PUBLICATIONS

GTITM UPOV ROM Citation for 'Barbara Harrington' QZ PBR 001735, Feb. 15, 2001.*
CPVO grant for Barbara Harrington.

* cited by examiner

*Primary Examiner*—Kent Bell
*Assistant Examiner*—Louanne Krawczewicz Myers
(74) *Attorney, Agent, or Firm*—Mark P. Bourgeois

(57) ABSTRACT

A new cultivar of *Clematis* named 'Barbara Harrington' that is characterized by intense deep purple flowers and a free flowering habit. In combination these traits set 'Barbara Harrington' apart from all other existing varieties of *Clematis* known to the inventor.

2 Drawing Sheets

Botanical classification: *Clematis* species.
Variety denomination: 'Barbara Harrington'.

BACKGROUND OF THE INVENTION

The present invention relates to a new and distinct cultivar of *Clematis,* a woody half climber that is grown for use in small gardens and for its cut flowers. The new cultivar is known botanically as a *Clematis* and will be referred to hereinafter by the cultivar name 'Barbara Harrington'.

'Barbara Harrington' was discovered by the inventor in 1996 in a cultivated area of Cambridgeshire, England. 'Barbara Harrington' was discovered as a single plant growing in a bed of *Clematis* 'Comtesse de Bouchard' (not patented). The exact parents are unknown.

The distinguishing characteristics of 'Barbara Harrington' are its intense deep purple color and free flowering habit. The closest comparison plants are *Clematis* 'Comtesse de Bouchard' and *Clematis* 'Ernest Markham' (not patented). 'Barbara Harrington' is distinguishable from *Clematis* 'Comtesse de Bouchard' by it's darker purple colored flower. The flowers of 'Comtesse de Bouchard' are a lighter purple. 'Barbara Harrington' is distinguishable from *Clematis* 'Ernest Markham' by having a more prolific flowering habit. 'Ernest Markham' does not flower prolifically.

'Barbara Harrington' was first asexually propagated by the inventor in Cambridgeshire, England in 1996 using softwood internodal cuttings. Since that time, under careful observation, the distinguishing characteristics have been determined stable and uniform in successive generations.

SUMMARY OF THE INVENTION

The following represent the distinguishing characteristics of the new *Clematis* cultivar 'Barbara Harrington'. In combination these traits set 'Barbara Harrington' apart from all other existing varieties of *Clematis* known to the inventor. 'Barbara Harrington' has not been tested under all possible conditions and phenotypic differences may be observed with variations in environmental, climatic, and cultural conditions, however, without any variance in genotype.

1. *Clematis* 'Barbara Harrington' is free flowering.
2. *Clematis* 'Barbara Harrington' exhibits an intense purple color
3. *Clematis* 'Barbara Harrington' is a climber that is hardy to USDA Zone 4.

BRIEF DESCRIPTION OF THE DRAWINGS

The accompanying color photographs illustrate the distinguishing traits of the new *Clematis* cultivar 'Barbara Harrington'. The plants in the photographs were grown out of doors in Cambridgeshire, England in ten liter containers.

The first drawing illustrates entire plants in bloom from a side perspective.

The second drawing is a close-up view of the leaves and a flower. All photographs are taken using conventional techniques and although foliage colors may appear different from actual colors due to light reflectance, they are as accurate as possible by conventional photography.

BOTANICAL DESCRIPTION OF THE PLANT

The following is a detailed description of the *Clematis* cultivar named 'Barbara Harrington'. Data was collected in Cambridgeshire, England, from 2 year old plants grown in ten liter containers outdoors. Color determinations are in accordance with The Royal Horticultural Society Colour Chart 2001 except where general color terms of ordinary dictionary significance are used. The growing requirements are similar to the species. Under normal growing conditions there are no known disease problems known to the inventor.

Botanical classification: *Clematis* 'Barbara Harrington'.
Common name: Virgins bower.
Uses: Ornamental garden climber.
Parent: 'Barbara Harrington' was discovered as a single plant growing in a crop of *Clematis* 'Comtesse de Bouchard' (not patented). The exact parents are unknown.
*Female parent.*—Unknown *Clematis.*
*Male parent.*—Unknown *Clematis.*

Type: Perennial.
Vigour: Vigorous.
Habit: Upright and scandent.
Height: 3.0 m. in height.
Width: 1.0 m. in width.
Hardiness: USDA Zone 4.
Disease resistance: Slightly susceptible to *clematis* wilt and powdery mildew.
Propagation: Softwood internodal cuttings.
Root system: Fibrous.
Soil: Plant in well-drained soils.
Sunlight: Plant in full sunlight.
Plant sexuality: Bisexual.
Time to initiate roots: 4 weeks are required for an initial cutting to produce roots at 20 degrees Centigrade.
Crop time: 12 months are required to produce a plant in 2 liter pots from a rooted cutting.
Seasonal interest: Flowers in spring and summer.
Stem:
*Branching habit.*—Upright.
*Internode length.*—10–15 cm. between nodes.
*Stem diameter.*—2.5 mm. in diameter.
*Stem length.*—2 m. in length.
*Shape.*—Furrowed.
*Surface.*—Pubescent on young shoots.
*Stem color.*—Young shoots are between 187A and 187B, Mature shoots are 178A on the ridges and 174A in the furrows.
Foliage:
*Type.*—Deciduous.
*Leaf arrangement.*—Opposite.
*Leaf division.*—Pinnate.
*Leaflet shape.*—Ovate.
*Leaflet base.*—Rounded.
*Leaflet apex.*—Acute.
*Leaf venation.*—Palmate.
*Vein color* (*adaxial surface*).—147A.
*Vein color* (*abaxial surface*).—147A.
*Leaf surface* (*adaxial*).—Sparsely pubescent.
*Leaf surface* (*abaxial*).—Sparsely pubescent.
*Leaf attachment.*—Petiolate.
*Petiole dimensions.*—66 mm. in length and 1.5 mm. in diameter, sparsely pubescent.
*Petiole color.*—200B.
*Leaf margin.*—Entire.
*Leaf length.*—187 mm.
*Leaf width.*—185 mm.
*Leaflet length.*—60 mm.
*Leaflet width.*—37 mm.
*Leaflet color* (*adaxial surface*).—147A.
*Leaflet color* (*abaxial surface*).—147A.
*Foliar fragrance.*—Absent.
Flower:
*Form.*—Terminal inflorescence.
*Inflorescence type.*—3 flowered cyme.
*Persistent or self-cleaning.*—Self-cleaning.
*Color of peduncle.*—187A.
*Peduncle length.*—98–122 mm.
*Peduncle diameter.*—2 mm.
*Surface of peduncle.*—Pubescent.
*Diameter of flower.*—118 mm. in diameter.
*Depth of flower.*—20 mm.
*Shape.*—Open campanulate.
*Sexuality.*—Bisexual.
*Aspect.*—Erect.
*Bud.*—Ovate.
*Bud length.*—37 mm.
*Bud diameter.*—14 mm.
*Bud color.*—77D.
*Petals.*—Apetalous.
*Tepals.*—Six in number.
*Color of tepals* (*upper surface*).—72A.
*Color of tepals* (*lower surface*).—77B.
*Tepal shape.*—Elliptic, concave in cross-section.
*Tepal apex.*—Mucronate.
*Tepal base.*—Cuneate.
*Tepal surface* (*upper*).—Rugose.
*Tepal surface* (*lower*).—Pubescent.
*Tepal margin.*—Sinuous.
*Tepal length.*—61 mm. in length.
*Tepal width.*—38 mm. in width.
*Unfused or fused.*—Tepals are unfused and overlap.
*Blooming period.*—End of June to the middle of September.
*Lastingness of individual bloom.*—10 to 20 days.
*Fragrance.*—None.
Reproduction organs:
*Stamen number.*—Greater than 60.
*Color of stamen filament.*—White.
*Dimensions of stamen.*—15 mm. in length and 1 mm in diameter.
*Dimensions of anther.*—1 mm. in width and 6 mm. in length.
*Anther color.*—6D.
*Pollen color.*—6D.
*Pollen quantity.*—Small.
*Pistil number.*—Greater than 50.
*Stigma color.*—160D.
*Stigma dimensions.*—10 mm. in length, 3 mm in width.
*Style color.*—160D.
*Ovary position.*—Superior.
*Ovary dimensions.*—Less than 1 mm.
Seed:
*Fertility.*—Self-sterile.
*Fruit.*—Single seed achenes, approximately 45 from each flower.
*Achene surface.*—Finely pubescent.
*Achene color.*—17A.
*Achene dimensions.*—6 mm. in width, 6 mm. in length, 1.5 mm in height.

It is claimed:

1. A new and distinct variety of *Clematis* plant named 'Barbara Harrington' as described and illustrated.

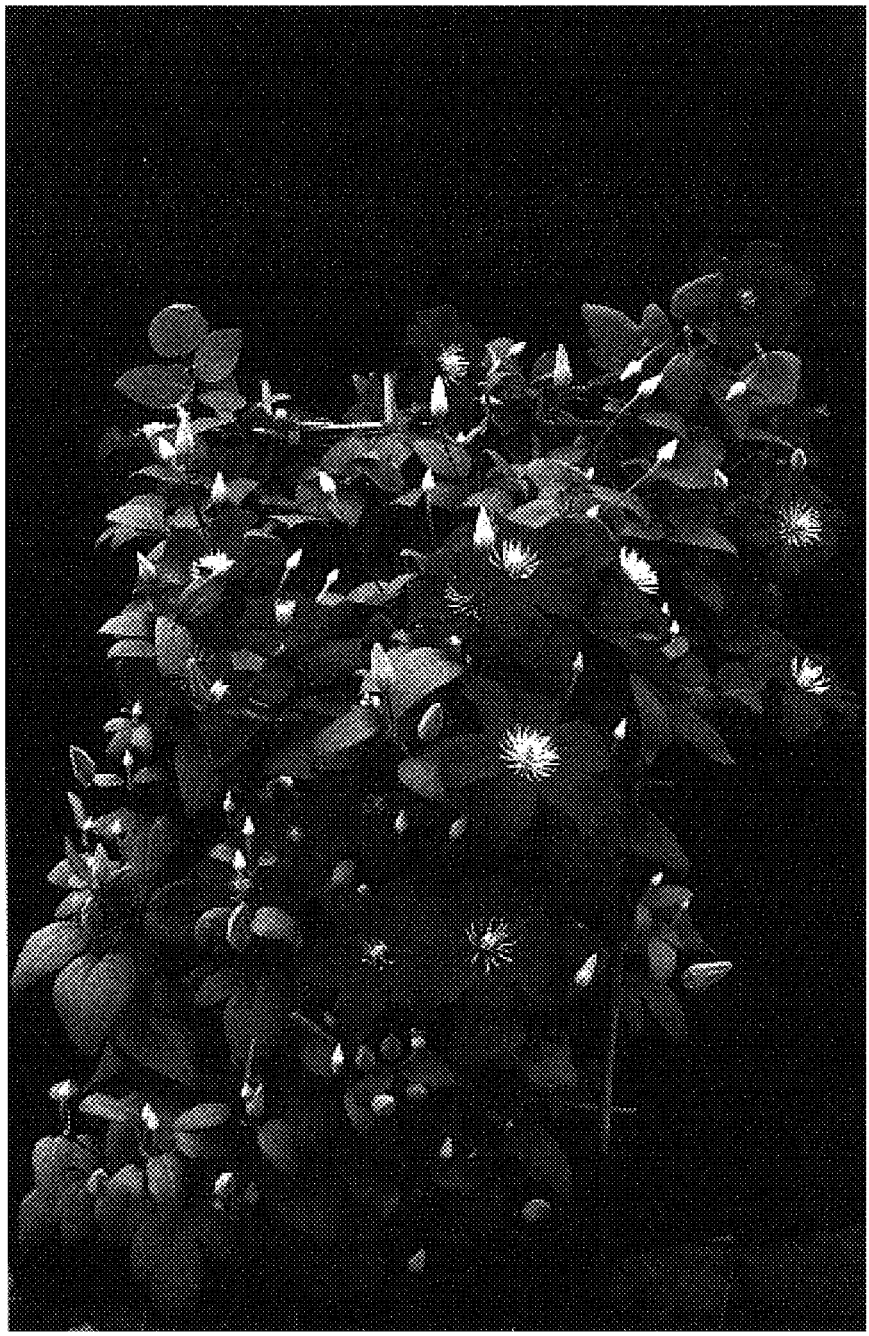

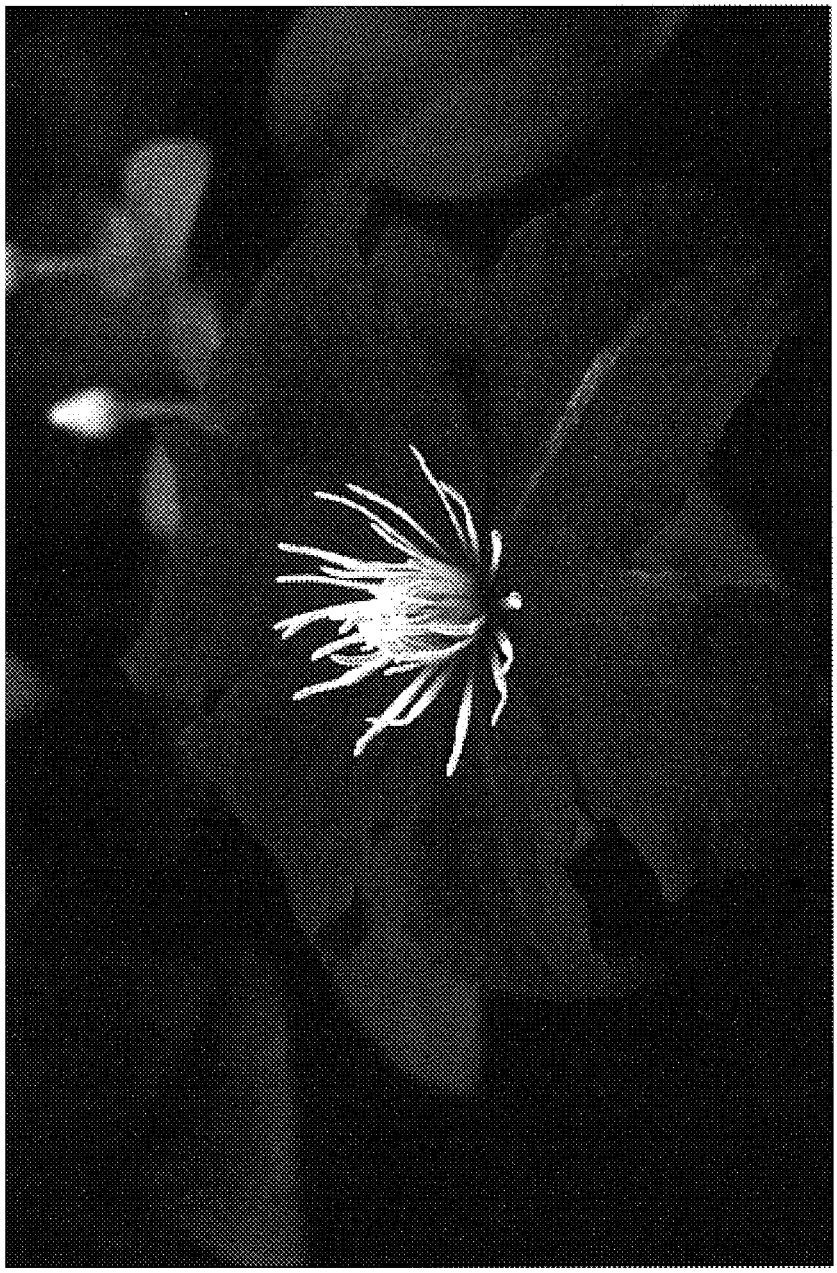

* * * * *